United States Patent [19]

Disteldorf et al.

[11] Patent Number: 4,668,780
[45] Date of Patent: May 26, 1987

[54] ISOCYANATE-URETDIONES AND A METHOD FOR THEIR PRODUCTION

[75] Inventors: Josef Disteldorf; Werner Hubel, both of Herne; Elmar Wolf, Recklinghausen, all of Fed. Rep. of Germany

[73] Assignee: Chemische Werke, Marl, Fed. Rep. of Germany

[21] Appl. No.: 822,965

[22] Filed: Jan. 28, 1986

Related U.S. Application Data

[63] Continuation of Ser. No. 511,930, Jul. 8, 1983, abandoned.

[30] Foreign Application Priority Data

Jul. 24, 1982 [DE] Fed. Rep. of Germany ....... 3227779

[51] Int. Cl.$^4$ ................. C07D 229/00; C07D 403/06; C07D 403/14
[52] U.S. Cl. .................................................... 540/202
[58] Field of Search ........................................ 540/202

[56] References Cited

U.S. PATENT DOCUMENTS 3,631,198 12/1971 Horuitz et al. ............. 260/453 AL
4,413,079 11/1983 Disteldorf et al. .................. 525/440
4,463,154 7/1984 Disteldorf et al. .................. 525/457
4,476,054 10/1984 Disteldorf et al. .................. 540/202

FOREIGN PATENT DOCUMENTS 1153815 5/1969 United Kingdom ........ 260/239 AR

OTHER PUBLICATIONS

Official Gazette, vol. 1047, No. 3, Oct. 16, 1984, p. 1019.

Primary Examiner—Donald G. Daus
Assistant Examiner—William A. Teoli, Jr.
Attorney, Agent, or Firm—Oblon, Fisher, Spivak, McClelland & Maier

[57] ABSTRACT

Isocyanate-uretdiones having the formula:

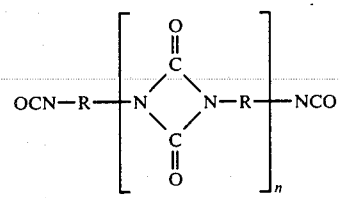

wherein the R groups are identical or different and are hydrocarbon groups having the formulas:

$$-CH_2-\underset{CH_3}{\underset{|}{\overset{H}{\overset{|}{C}}}}-CH_2-CH_2-CH_2- \text{ or } -CH_2-CH_2-\underset{CH_2CH_3}{\underset{|}{\overset{H}{\overset{|}{C}}}}-CH_2-$$

and n is an integral or fractional number from 1 to 5.

Production of the isocyanate-uretdiones, which can be dissociated by heat up to an extent of greater than 70%, is accomplished through dimerization of aliphatic diisocyanates having the formula:

$$OCN-CH_2-\underset{CH_3}{\underset{|}{\overset{H}{\overset{|}{C}}}}-CH_2-CH_2-CH_2-NCO \quad \text{or}$$

$$OCN-CH_2-\underset{CH_2CH_3}{\underset{|}{\overset{H}{\overset{|}{C}}}}-CH_2-CH_2-NCO$$

with a phosphine catalyst having the formula:

$X_mP(NR_2)_{3-m}$ wherein:
m is 0, 1 or 2;
x is a —Cl, —OR or —R group, wherein R is identical or different alkyl-, arylalkyl-, cycloalkyl, or alkyl-substituted cycloalkyl groups. The reaction temperatures are 0°–80° C.
The reaction product is subjected to thin-layer distillation after a conversion of 5–70%, by weight, without deactivation of the catalyst. The compounds of the present invention are useful as intermediates in the production of starting materials for the production of polyurethanes.

10 Claims, No Drawings

ISOCYANATE-URETDIONES AND A METHOD FOR THEIR PRODUCTION

This application is a continuation of application Ser. No. 511,930, filed July 8, 1983, now abandoned.

BACKGROUND OF THE INVENTION

1. Field of the Invention:

This invention relates to isocyanate-uretdione compounds and a method for their production.

2. Description of the Prior Art:

Aromatically substituted uretdiones, and their production through the dimerization of aromatic isocyanates with tertiary amines or phosphines as catalysts, have been known for a long time. Surprisingly enough, however, aliphatically substituted uretdiones were described for the first time in DE-OS No. 16 70 720.

The aliphatic uretdiones prepared according to the teaching of DE-OS No. 16 70 720, to be sure, contain a considerable amount of the corresponding isocyanurates as an impurity. For example, aliphatic uretdiones prepared according to Examples 1, 2a, 2b and 2c contain 40% butylisocyanurate, 49% ethylisocyanurate, 59% ethylisocyanurate, and 79% ethylisocyanurate, respectively, as impurities.

Further, experiments involving the dimerization of 2-methyl-1,5-diisocyanate-pentane (MPDI), which, if necessary may contain up to 12% by weight of 2-ethyl-1,4-diisocyanate-butane (EBDI), according to the method described in DE-OS No. 16 70 720, led to a reaction mixture having a content of uretdione of only about 30%, by weight.

The oligomerization product of 2-methyl-1,5-diisocyanate-pentane (MPDI) having a high content of dimers has significant utility in the subsequent reaction with diol compounds for the manufacture of valuable starting materials for polyurethane chemistry. However, to date such a product has not been attained.

Therefore, a need continues to exist for such uretdione compounds which have a high uretdione content and a relatively low content of impurities.

SUMMARY OF THE INVENTION

Accordingly, it is an object of the present invention to provide uretdione compounds which have a high uretdione content.

It is also an object of this invention to provide uretdione compounds which may be readily dissociated into the starting monomers to a large extent.

Moreover, it is another object of the present invention to provide a method for producing such uretdione compounds.

According to the present invention, the foregoing and other objects are attained by providing an isocynate-uretdione compound having the formula:

$$\left[ OCN-R-N\underset{\underset{O}{\overset{\|}{C}}}{\overset{\overset{O}{\overset{\|}{C}}}{\diagup\hspace{-0.5em}\diagdown}}N-R-NCO \right]_n$$

wherein the groups R comprise a hydrocarbon group having the formula:

$$-CH_2-\underset{\underset{CH_3}{|}}{\overset{\overset{H}{|}}{C}}-CH_2-CH_2-CH_2- \text{ or } -CH_2-CH_2-\underset{\underset{CH_2CH_3}{|}}{\overset{\overset{H}{|}}{C}}-CH_2-$$

and n is an integral or fractional number from 1 to 5; and a process for preparing the same.

DETAILED DESCRIPTION OF THE PREFERRED EMBODIMENTS

According to the invention, an isocyanate-uretdione is produced which by heating may be readily dissociated into the starting isocyanate monomers to the extent of more than 70%.

The isocyanate-uretdione of the present invention has the formula:

$$\left[ OCN-R-N\underset{\underset{O}{\overset{\|}{C}}}{\overset{\overset{O}{\overset{\|}{C}}}{\diagup\hspace{-0.5em}\diagdown}}N-R-NCO \right]_n$$

wherein the groups R are identical to or different from each other and are hydrocarbon groups having the formula:

$$-CH_2-\underset{\underset{CH_3}{|}}{\overset{\overset{H}{|}}{C}}-CH_2-CH_2-CH_2- \text{ or } -CH_2-CH_2-\underset{\underset{CH_2CH_3}{|}}{\overset{\overset{H}{|}}{C}}-CH_2-$$

and n is an integral or fractional number from 1 to 5. The isocynate-uretdione compound is obtained by the catalytic dimerization of a part of the isocyanate groups of aliphatic diisocyanate compounds.

As the aliphatic diisocyanate compound, diisocyanates having the formula:

$$OCN-CH_2-\underset{\underset{CH_3}{|}}{\overset{\overset{H}{|}}{C}}-CH_2-CH_2-CH_2-NCO \quad (MPDI) \text{ or}$$

$$OCN-CH_2-\underset{\underset{CH_2CH_3}{|}}{\overset{\overset{H}{|}}{C}}-CH_2-CH_2-NCO \quad (EBDI)$$

are used in the present invention. A mixture of these diisocyanates may also be used.

As a catalyst, a compound having the formula:

$$X_mP(NR_2)_{3-m}$$

is used, wherein m is 0, 1 or 2; X is —Cl, —Or or R groups, wherein R is identical or different alkyl, arylalkyl, cycloalkyl or alkyl-substituted cycloalkyl groups.

The aliphatic diisocyanates listed above, (MPDI) and (EBDI) are dimerized in the presence of the catalyst at temperatures of 0°–80° C., preferably, 10°–30° C., until the diisocyanate or diisocyanates are converted to 5–70%, by weight, of dimer product. It is preferred, however, to continue the dimerization with the aid of a catalyst until the diisocyante or diisocyanates are converted to 30–60%, by weight, of dimer product.

The dimer product is isolated from the reaction mixture, without prior deactivation of the catalyst, through thin-layer distillation, whereby the dimer product is obtained as a residue and the monomer or monomers and catalyst are recovered as a distillate.

The catalysts are used in quantities of 0.1–5%, by weight, preferably 0.5–2%, by weight. Particularly suitable as the catalyst is tris-[dimethylamino]phosphine. The production of phosphorous compounds such as this compound is described in Houben-Weyl, Volume V, page 108.

Generally, the diisocyanate mixtures used in the method of the present invention have the following composition:
88–99% by weight of 2-methyl-1,5-diisocyanate-pentane (MPDI)
12 to 1% by weight of 2-ethyl-1,4-diisocyanate-butane (EBDI).
Pure (MPDI) may also be used instead of a mixture.

The preferred initial diisocyanate is a diisocyanate mixture consisting of about 88–95% by weight of 2-methyl-1,5-diisocyanate-pentane and 12 to 5% by weight of 2-ethyl-1,4-diisocyanate-butane.

The production of diisocyanates or diisocyanate mixtures is accomplished in the known manner through the phosgenization of the corresponding diamines (see, for example, U.S. Pat. No. 3,631,198). The latter may be obtained by catalytic hydrogenation of the corresponding dinitriles which, are obtained as byproducts during the production of adipodinitrile by the reaction butadiene with HCN or during the dimerization of acrylonitrile.

The method according to the invention is carried out in two steps, wherein:

(a) A diisocyanate or diisocyanate mixture is converted to 5–70%, by weight, preferably 30–60%, by weight, of dimer product with the aid of a catalyst, and (b) the unreacted diisocyanate or diisocyanate mixture is separated from the reaction product through thin-layer distillation.

The distilled MPDI, possibly with EBDI and catalyst, may be used again for reaction.

The reaction temperature is in the range of 10° to 80° C., preferably 10° to 30° C. The required amount of catalyst depends on the type of catalyst used. Quantities ranging from 0.1–5% by weight, based on the MPDI or MPDI/EBDI mixture, are generally adequate. It is preferably to use 0.5 to 2% by weight of phosphorous anhydride triamides. The reaction time, during which, for example, 30–60% by weight of MPDI (or MPDI in a mixture with EBDI) is converted will, at contant temperature, depend on the concentration and the type of the catalyst used to a large degree. Typically, the reaction time is 3–40 hours. The reaction may be carried out in polar solvents such as esters, chlorinated hydrocarbons, ethers, and ketones, or may be run solvent-free. It is preferable to carry out the reaction solvent-free.

The reaction mixture is processed by thin-layer distillation at 100°–120° C. and 0.01–0.5 mm Hg.

The reaction products of the present invention have low viscosity at room temperature (about 700–1200 mPas). Their isocyanate (NCO) content is between about 18 and 23% by weight, preferably 20–22% by weight. In other words, it is necessary to have large portions of oligomeric uretdiones (or, to a lesser degree, also isocyanurates) of MPDI and/or EBDI in the reaction product.

The monomer content of the reaction product is less than 1%; after heating to 180°–200° C. (0.5 hour), the NCO content is 42–44% by weight.

The uretdione of MPDI or a MPDI/EBDI mixture is used as an intermediate product for making synthetic substances, lacquers, and foam materials. Blocked with blocking agents, such as ε-caprolactam or acetoxime, the uretdione mixture is suitable for the manufacture of solvent-containing and solvent-free, single-component and two-component lacquers, such as, coil-coating and high-solid lacquers and polyurethane powder lacquers.

The present invention will be further illustrated by certain examples and references which are provided for purposes of illustration only and are not intended to limit the present invention.

EXAMPLE 1

(Comparison Example)

1,000 parts by weight of 2-methyl-1,5-diisocyanate-pentane (with about 6% 2-ethyl-1, 4-diisocyanate-butane) and 10 parts by weight of tributylphosphine were allowed to stand at room temperature for 3 hours. After that time, the NCO content dropped from 50% to about 38%. Without prior deactivation of the catalyst, the reaction mixture was distilled at 150° C./0.1 mm Hg in the thin-layer evaporator. The residue had an NCO content of 20.5%; upon heating to 180° C. for 30 minutes, an NCO content of 36.5% was observed.

EXAMPLE 2

1,000 parts by weight of MPDI (with about 6% EBDI) and 10 parts by weight of tris-(dimethylamino)-phosphine were allowed to stand at room temperature for 2 hours. After that time, the NCO content of the reaction mixture was 39.3%. The reaction mixture was distilled as in Example 1.

The residue at 25° C. had a viscosity of 165 mPas and an NCO content of 20.3%; upon heating to 180° C. for 30 minutes, an NCO content of 46.3% was observed. The IR spectrum of the residue is shown in FIG. 1.

EXAMPLE 3

1,000 parts by weight of MPDI (with about 6% EBDI) and 15 parts by weight of phosphorous acid(bis-dimethylamide)-chloride were allowed to stand at room temperature for 6 hours. After that time, the NCO content of the reaction mixture was 37%. The reaction mixture was distilled as in Example 1. The residue contained 20.1% NCO; upon heating to 180° C. for 30 minutes, an NCO content of 43.8% was observed.

EXAMPLE 4

1,000 parts by weight of MPDI (with about 6% EBDI) and 10 parts by weight of phosphorous acid methylesterbis-diethylamide were allowed to stand at room temperature for 10 hours. After that time, the NCO content of the reaction mixture was 36.5%. The reaction mixture was distilled as in Example 1. The residue contained 20.0% NCO; upon heating to 180° C. for 30 minutes, an NCO content of 44% was found.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for preparing an isocyanate-uretdione having a uretdione content of at least about 85% having the formula:

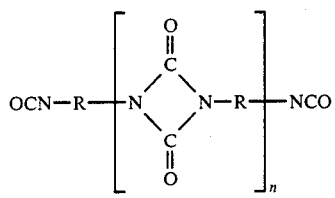

wherein the R groups are identical to or different from each other and consist essentially of hydrocarbon groups having the formula:

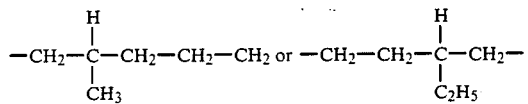

wherein n is an integral or fractional number from 1 to 5, which comprises:

(a) dimerizing some of the isocyanate groups of an aliphatic diisocyanate compound having the formula:

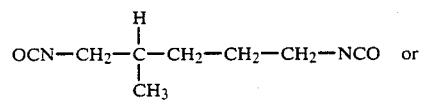

-continued

OCN—CH$_2$—C(H)(CH$_2$CH$_3$)—CH$_2$—CH$_2$—NCO or a mixture thereof, in the presence of a catalyst compound having the formula:

$$X_mP(NR_2)_{3-m}$$

wherein m is 0, 1 or 2; x is a —Cl, —OR or R group, wherein R is identical or different alkyl, aralkyl or alkyl-substituted cycloalkyl groups, at a temperature in the range of 0°–80° C., such that said aliphatic diisocyanate or diisocyanate mixture is converted to 5–70% by weight of said isocyanate-uretdione; and (b) isolating said isocyanate-uretdione from the reaction mixture without prior deactivation of said catalyst.

2. A method according to claim 1, wherein said dimerization is effected at a temperature in the range of 10°–30° C.

3. The method according to claim 1, wherein R of said catalyst is a lower alkyl group.

4. The method according to claim 1, wherein said isocyanate-uretdione is capable of readily dissociating to an extent of greater than 70% into said aliphatic diisocyanate compound or compounds.

5. The method according to claim 1, wherein said diisocyanate or diisocyanate mixture is dimerized such that about 30–60%, by weight, of said diisocyanate or diisocyanate mixture is converted to said isocyanate-uretdione.

6. The method according to claim 1, wherein said catalyst is used in the amount of 0.1 to 5% by weight.

7. The method according to claim 1, wherein said catalyst is tris-phosphine.

8. The method according to claim 1, wherein said isocyanate-uretdione is isolated from the reaction mixture by thin-layer distillation at 100°–120° C. and 0.01–0.5 mm Hg.

9. The method according to claim 1, wherein the dimerization with the aid of said catalyst is conducted at a temperature of 10° to 30° C.

10. The method according to claim 6, wherein said catalyst is used in the amount of 0.5–2% by weight.

* * * * *